(12) United States Patent
Shapland

(10) Patent No.: US 9,345,843 B2
(45) Date of Patent: May 24, 2016

(54) UNIVERSAL ADAPTOR

(76) Inventor: Howard Shapland, Woodton (GB)

( * ) Notice: Subject to any disclaimer, the term of this patent is extended or adjusted under 35 U.S.C. 154(b) by 268 days.

(21) Appl. No.: 13/384,443

(22) PCT Filed: Jul. 15, 2010

(86) PCT No.: PCT/GB2010/051160
§ 371 (c)(1),
(2), (4) Date: Feb. 6, 2012

(87) PCT Pub. No.: WO2011/007178
PCT Pub. Date: Jan. 20, 2011

(65) Prior Publication Data
US 2012/0130277 A1 May 24, 2012

(30) Foreign Application Priority Data
Jul. 16, 2009 (GB) .................................. 0912347.2

(51) Int. Cl.
A61M 5/32 (2006.01)

(52) U.S. Cl.
CPC ........ *A61M 5/3269* (2013.01); *A61M 2005/325* (2013.01)

(58) Field of Classification Search
CPC ... A61M 5/00; A61M 5/32; A61M 2005/325; A61M 5/3269
USPC .......... 600/576, 573; 604/110, 187, 192, 198, 604/208–210, 263
See application file for complete search history.

(56) References Cited

U.S. PATENT DOCUMENTS

| 4,790,828 | A | * | 12/1988 | Dombrowski et al. ....... 604/198 |
| 4,892,521 | A | | 1/1990 | Laico et al. |
| 4,955,866 | A | * | 9/1990 | Corey ........................... 604/192 |
| 5,163,916 | A | * | 11/1992 | Sunderland ................... 604/198 |
| 5,195,982 | A | * | 3/1993 | Hoenig ......................... 604/192 |
| 5,222,945 | A | * | 6/1993 | Basnight ....................... 604/110 |
| 5,312,367 | A | * | 5/1994 | Nathan ......................... 604/192 |
| 5,342,320 | A | * | 8/1994 | Cameron ...................... 604/192 |
| 5,445,618 | A | * | 8/1995 | Adobbati ...................... 604/192 |
| 5,466,223 | A | * | 11/1995 | Bressler et al. ............... 604/110 |
| 5,501,674 | A | * | 3/1996 | Trombley et al. ............. 604/247 |
| 5,630,803 | A | | 5/1997 | Tamaro |
| 5,672,161 | A | * | 9/1997 | Allen et al. ................... 604/263 |
| 5,688,249 | A | * | 11/1997 | Chang et al. .................. 604/198 |
| 5,779,684 | A | | 7/1998 | Tamaro |

(Continued)

FOREIGN PATENT DOCUMENTS

EP 1350529 A1 10/2003
JP P2003299735 A 10/2003

(Continued)

*Primary Examiner* — Rene Towa
(74) *Attorney, Agent, or Firm* — Brinks Gilson & Lione; G. Peter Nichols

(57) ABSTRACT

A needle safety lock comprising a needle guard supporting member (14), and a needle guard (16) comprising an elongate member coupled to said needle guard supporting member and axially slideable with respect to the needle guard supporting member, and a cylindrical guard (20) having two open ends to enclose at least a portion of a needle; wherein the needle guard comprises a locking means to selectively secure the needle guard in a first locking position that is releasable or a second locking position that is non-releasable; and wherein when the needle guard is in the first or second locking position free axial movement of the needle guard is prevented.

15 Claims, 11 Drawing Sheets

(56) References Cited

U.S. PATENT DOCUMENTS

| | | | |
|---|---|---|---|
| 5,792,121 A | 8/1998 | Tamaro | |
| 5,807,352 A | 9/1998 | Tamaro | |
| 5,810,784 A | 9/1998 | Tamaro | |
| 5,817,070 A | 10/1998 | Tamaro | |
| 5,879,337 A * | 3/1999 | Kuracina et al. | 604/192 |
| 6,149,629 A * | 11/2000 | Wilson et al. | 604/198 |
| 6,213,987 B1 * | 4/2001 | Hirsch et al. | 604/263 |
| 6,280,460 B1 * | 8/2001 | Bolduc et al. | 606/222 |
| 6,287,278 B1 * | 9/2001 | Woehr et al. | 604/110 |
| 7,214,208 B2 * | 5/2007 | Vaillancourt et al. | 604/110 |
| 7,393,345 B2 * | 7/2008 | Yang | 604/199 |
| 7,481,797 B2 * | 1/2009 | Mahurkar | 604/195 |
| 7,534,231 B2 * | 5/2009 | Kuracina et al. | 604/192 |
| 2002/0165498 A1 | 11/2002 | Ward, Jr. | |
| 2003/0028171 A1 | 2/2003 | Deharde | |
| 2003/0229316 A1 * | 12/2003 | Hwang et al. | 604/263 |
| 2005/0187493 A1 * | 8/2005 | Swenson et al. | 600/576 |
| 2005/0192545 A1 * | 9/2005 | Voorhees et al. | 604/263 |
| 2006/0189934 A1 * | 8/2006 | Kuracina et al. | 604/110 |
| 2007/0088261 A1 * | 4/2007 | Lew et al. | 604/110 |
| 2007/0167917 A1 * | 7/2007 | Lee | 604/187 |

FOREIGN PATENT DOCUMENTS

| | | |
|---|---|---|
| WO | 03103755 A2 | 12/2003 |
| WO | 2006041442 A1 | 4/2006 |
| WO | 2006072135 A1 | 7/2006 |
| WO | 2006072807 A1 | 7/2006 |
| WO | 2006074121 A2 | 7/2006 |
| WO | 2006082350 A1 | 8/2006 |
| WO | 2006127484 A1 | 11/2006 |
| WO | 2006130181 A2 | 12/2006 |
| WO | 2006131832 A1 | 12/2006 |
| WO | 2006135617 A2 | 12/2006 |
| WO | 2007003702 A1 | 1/2007 |
| WO | 2007072119 A1 | 6/2007 |
| WO | 2007077463 A1 | 7/2007 |
| WO | 2007082226 A1 | 7/2007 |
| WO | 2008033334 A2 | 3/2008 |

* cited by examiner

UNIVERSAL ADAPTOR

FIELD OF THE INVENTION

The present invention relates to a universal needle safety lock for use in preventing needlestick injuries.

BACKGROUND OF THE INVENTION

The medical community has been aware of the problem of needlestick injuries for years but only with the advent of HIV AIDS and the discovery of Hepatitis C virus in the 1980s did this problem become a burning issue. The infectivity of blood borne pathogens via needlestick injuries then came into focus. Even so, little progress has been made in the past 20 years.

In some countries, as many as 90% of the injections given are unsafe. Furthermore, 21 million people in developing countries around the world are infected yearly from contaminated syringes (WHO: Immunisation safety priority project, 1999-2005). As a result of needlestick injuries, more than 580 million people in the world are chronic carriers of diseases, and an estimated 1.3 to 1.6 million people die annually.

In the U.S. alone, 1 million healthcare workers have been stuck with hypodermic needles that may be infected with Hepatitis B, Hepatitis C or HIV. Over a thousand of these healthcare workers contracted a serious infection, 80% of which could have been prevented by using appropriate safety devices. As a result, a total of $3 billion per year is spent in the U.S. on needlestick injuries.

In the U.K., an ongoing Royal College of Nursing surveillance project suggests that as many as 100,000 needlestick accidents occur every year. There are currently 12 cases of HIV infection among NHS workers in the U.K. that are suspected to have been caused by needlestick injuries. As a result, needlestick injuries are estimated to cost each NHS trust around £500,000 per year.

The solution to the problem of needlestick injuries is the introduction of medical devices with an engineered safety solution along with adequate training of personnel and the application of universal precautions.

WO 2006/072135 describes a safety device for a needle and syringe comprising a shield that is slideably attached to the body of a syringe and that can be moved between a retracted and shielding position to shield a needle tip. However, the device disclosed in this application must be operated with two hands. Furthermore, in order to retract the shield to expose the needle for use, the user is required to place their hands close to the needle tip. In addition, when the shield is fully retracted and the needle exposed—i.e. the position required for use of the device, the shield fully or partially covers the syringe. As a result, it is difficult for the user to read the scales present on the syringe due to the presence of the shield. A final limitation of this device is that due to its size, the device will take up more room in expensive sharps containers.

Other needle safety devices include that disclosed in US2002/0165498, which describes a safety needle assembly comprising a needle, a spring-driven shield assembly and a safety cap, wherein the shield assembly comprises a plurality of arms that allow sliding of the shield from a retracted to an extended position. However, in order to extend the shield over the needle the user is required to alter their grip, from the position required to operate the needle, to the position required to push against one of the arms of the shield assembly. As a consequence, actuation requires the user to place a thumb or finger in close proximity to the needle tip.

In addition to the above, the above-described devices require the user to retract the device from the injection site thereby exposing the needle before actuation.

EP1350529 describes a safety shield assembly for an intravenous apparatus, wherein the shield comprises a forward shield, a guide element and a locking member. The forward shield comprises a distal blunting end that has a distal aperture and a proximal needle passageway. In the closed position, the needle tip is covered by the distal blunting end. However, the device described in this application is limited to use with blood collection or intravenous infusion devices.

Therefore there exists a need for a needle safety device that can be operated single-handedly and where the user can operate the device without a change in grip and while maintaining hands and fingers safely behind the needle tip. Furthermore, given the high demand for such devices in health services, it is important that such a device can be cheaply and easily produced and has cheap disposal costs. There also exists a need for a needle safety device that can be universally used with a range of medical devices from staked needle syringes to blood collection needles, hypodermic needles and other hollow bore needle devices.

SUMMARY OF THE INVENTION

In accordance with a first aspect of the present invention there is provided a needle safety lock comprising a needle guard supporting member; and a needle guard comprising an elongate member coupled to said guard supporting member and axially slideable with respect to the guard supporting member, and a cylindrical guard having two open ends to enclose at least a portion of a needle; wherein the needle guard comprises a locking means to selectively secure the needle guard in a first locking position that is releasable or a second locking position that is non-releasable, wherein when the needle guard is in the first or second locking position free axial movement of the needle guard is prevented.

In another aspect of the invention there is provided a needle safety device comprising a needle having a needle tip and hub; a needle guard supporting member; and a needle guard comprising an elongate member coupled with said needle guard supporting member and axially slideable with respect to the guard supporting member, and a cylindrical guard enclosing at least a portion of said needle, said cylindrical guard having two open ends such that the cylindrical guard is axially slideable along the length of the needle; and wherein the needle guard comprises a locking means to selectively secure the needle guard in a first locking position that is releasable or a second locking position that is non-releasable, wherein when the needle guard is in the first or second locking position free axial movement of the needle guard is prevented. In this aspect, the needle guard is axially slideable with respect to the needle from a first position wherein the needle tip is exposed to a second position wherein the needle tip is covered.

In a further aspect of the present invention there is provided a needle safety device as described above further comprising an injecting or collector means. The injecting means may comprise a syringe. Most preferably the syringe may be a prefilled 'staked needle syringe'. The collecting means may comprise a blood collection needle holder or intravenous line. A key aspect of this invention is that the device can be used with a range of different injecting or collecting means, of different shapes and volumes.

The elongate member of the present invention may be L-shaped although other shapes may be used. The length of the elongate member may be at least the length of the needle, although in a preferred embodiment, the length of the elongate member is longer than the length of the needle.

The needle of the present invention may be a hypodermic needle, a tuohy needle, a multi-sample blood collection needle or any other suitable needle. The needle may be connected to any of the above listed injecting or collecting means. The needle and injecting or collecting means may be connected by a luer lock, but other means of connection will be known to the skilled person. A key aspect of this invention is that the device can be used with a range of different needles.

In one embodiment the needle guard supporting member engages with the hub of the needle. In another alternative embodiment, the needle guard supporting member engages with the collecting or injecting means. In a preferred embodiment, the needle guard supporting member engages with a syringe. Most preferably a staked needle syringe. The needle guard supporting member may also be detachably mounted to the needle or injecting or collecting means. In one embodiment, the guard supporting member is able to open to receive a syringe. This may be achieved by providing a hinge on one portion of the guard supporting member. Accordingly, in use, the hinge on the guard supporting member allows the guard supporting member to be opened along its longitudinal axis and subsequently closed around an injecting or collecting means such as a syringe. In an alternative embodiment the guard supporting member is fixed to the needle hub or collecting or injecting means. The guard supporting member may be fixed by adhesives, interference fit or ultra sonic or high frequency (RF) welding. In a further embodiment, the guard supporting member may be coloured. In a preferred embodiment the guard supporting member is of a different colour to the needle guard. In another preferred embodiment the guard supporting member may be one of many different colours to indicate its compatibility with different needles or collecting/injecting devices. In a further aspect of the present invention the needle guard supporting member comprises a tamper evident labeling panel.

In one embodiment of the invention, the locking means comprises a combination of engageable projections and recesses on the elongate member and needle guard supporting member. In a preferred embodiment the locking means comprises a projection on the needle guard supporting member and a corresponding recess on the elongate member of the needle guard. The recess may be proximally positioned on the elongate member. In an alternative embodiment, the locking means comprises a projection on the elongate member and a recess on the needle guard supporting member. The projection may be proximally positioned on the elongate member.

In a further embodiment of the invention the elongate member comprises at least one, preferably two recesses or projections. In a preferred embodiment, the elongate member comprises a first and second recess engageable with a corresponding projection on the needle guard supporting member. The combination of two recesses on the elongate member and the projection on the needle guard supporting member comprise the two locking positions. The position of the needle guard in either the first or second locking position corresponds with the position of the needle guard in the second position, i.e. where the needle tip is covered by the needle guard. In this embodiment, both recesses are proximally positioned on the elongate member, and the second recess is proximally spaced from the first recess. The first and second recesses are arranged such that the first recess restricts axial movement of the needle guard up to application of a first predefined force, and the second recess restricts axial movement up to a second greater predefined force.

The first locking position is provided by interaction between the first recess and the projection. This locking position is retractable, such that the user can retract the needle guard to re-expose the needle tip. However, upon further distal movement of the needle guard, the projection on the needle guard supporting member engages with the second recess on the elongate member. This engagement constitutes the second locking position. Engagement of the second recess and projection prevents axial movement of the needle guard in either direction and effectively locks the needle from further use.

The recesses may be of different depths. In a preferred embodiment, the second recess is deeper than the first recess. The recesses may also be of different shapes. In a preferred embodiment the recesses may be rectangular in shape, although other shapes, regular and irregular, may be used. The recesses may also comprise angled or stepped surfaces. Preferably, the first recess has a wedge-shaped angled surface to allow the projection to disengage from the recess. Preferably, the second recess has a substantially vertical surface so that the projection cannot disengage from the recess. The second recess may also further comprise a protrusion to prevent tampering.

In a further embodiment, engagement of at least the second recess, preferably the first and second recess with the projection on the needle guard supporting member results in a sound, such as a click on registration that notifies the user that the needle tip is covered.

In an alternative aspect of the present invention the cylindrical guard further comprises a resilient member. The resilient member can move between an inactive position and an active position. In the active position the resilient member engages with the tip of the needle to prevent further distal movement of the needle. In the context of the needle assembly, the resilient member moves into the active position when the needle guard is in the second position—that is when the needle tip is covered by the needle guard and when the needle guard and guard supporting member is in the locked position—preferably the second locked position. In addition, the resilient member in the active position also ensures that the tip of the needle is always inaccessible when the needle guard device is locked.

The needle guard also preferably further comprises a disengagement means. The disengagement means can be used to disengage the elongate member from the needle guard supporting member to allow axial movement of the needle guard. In a preferred embodiment, the disengagement means allows disengagement of the first recess on the elongate member from the projection on the needle guard supporting member. The disengagement means may be proximally positioned on the elongate member. In a preferred embodiment, the disengagement means comprises a finger-shaped groove on the elongate member, wherein in use, application of digital pressure to the finger-shaped groove in a proximal or distal direction causes disengagement of the first recess from the projection to restore axial movement of the needle guard. The finger shaped groove may also be used to move the needle guard from the first position to the second position.

The invention also provides a needle assembly further comprising packaging and instructions for use of the needle assembly.

The device of the present invention is preferably manufactured from a plastics material. The material may be transparent or opaque. Most preferably the device of the present invention is polypropylene or nylon.

The device of the present invention can be used as follows. In the retracted state where the needle guard is in the first position and the needle tip is exposed, the elongate member of the needle guard will be proximally displaced relative to the needle assembly, such that the cylindrical guard is proximal to the needle hub. From this position, the user can extend the needle guard so that the cylindrical guard covers the needle tip. The needle guard can be extended using the finger shaped groove positioned on the proximal end of the elongate member. The length of the elongate member is at least equal in length, preferably longer, than the length of the needle. Accordingly, when fully extending the needle guard to cover the needle tip the user can maintain their hands and fingers safely behind the needle hub. Furthermore, the presence of the finger shaped groove of the elongate member of the needle guard allows the user to extend the needle guard to its second position single-handedly and without a change in grip from that used to operate the syringe.

Furthermore, the device of the present invention is comprised of two engageable parts—the needle guard and the needle guard supporting member. Accordingly, the device can be easily assembled and adapted to fit a large range of needles and injecting or collecting devices. In particular, in one embodiment of the present invention the needle guard supporting member can be retro-fitted to a connected syringe so not only can elements of the needle guard safety device be reused, but the needle guard can be fitted to conventional syringes or other injecting or collecting devices without the need for specific manufacture of the complete needle assembly.

Therefore, not only are the manufacturing costs for this device low but so are the disposal costs and thus this device is a realistic option for use in health services.

In addition to the above, the device of the present invention will work identically across all ranges of needles. This will make the training of health care professionals and subsequent integration into clinical use easier.

DETAILED DESCRIPTION OF THE DRAWINGS

Figure 1:
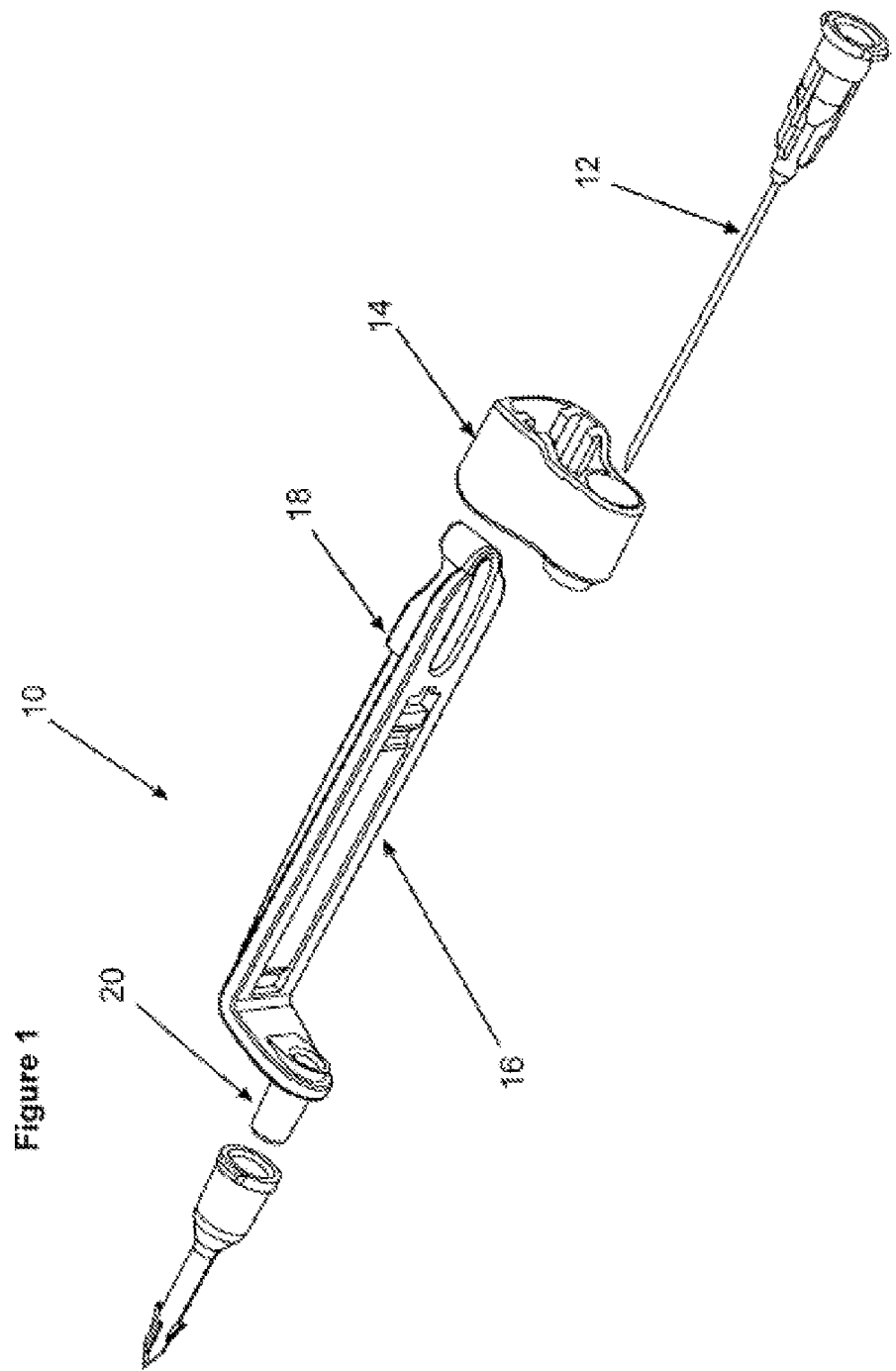
FIG. 1 shows a side view of one embodiment of the needle safety device of the present invention.

Referring to the drawings, FIG. 1 shows a side view of one embodiment of a needle guard safety device 10 according to the present invention, comprising a needle 12 having a distal needle tip and proximal hub, a needle guard supporting member 14, a needle guard 16 comprising an elongate member 18 and a cylindrical guard 20.

Figure 2:
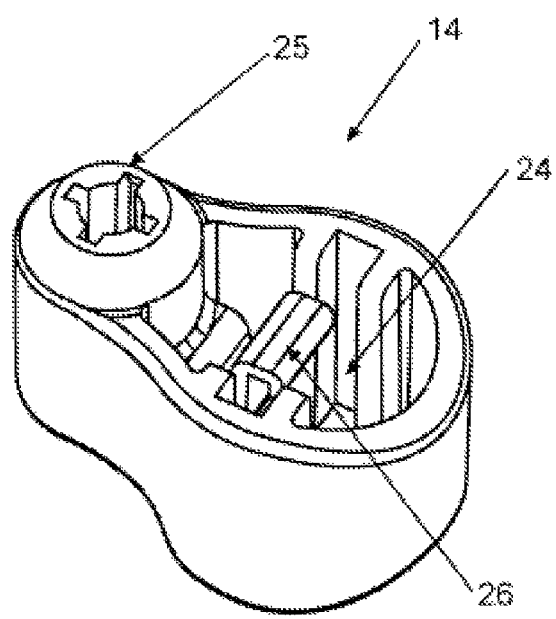
FIG. 2 shows a perspective view of one embodiment of the needle guard supporting member.

FIG. 2 shows a perspective view of a needle guard supporting member 14 according to one embodiment of the present invention. The needle guard supporting member 14 comprises two apertures 24 and 25 configured to engage with the elongate member of the needle guard (not shown) and the hub of a needle (also not shown) respectively. In this figure aperture 25 is configured to engage with the hub of a hypodermic needle. In an alternative embodiment aperture 25 is configured to engage with a blood collection needle (not shown). The needle supporting member 14 may further comprise a projection 26. The projection 26 is positioned to engage with a recess on the underside of the elongate member (not shown). The projection may be L-shaped, or wedge-shaped. More preferably the projection is L-shaped.

Figure 3:
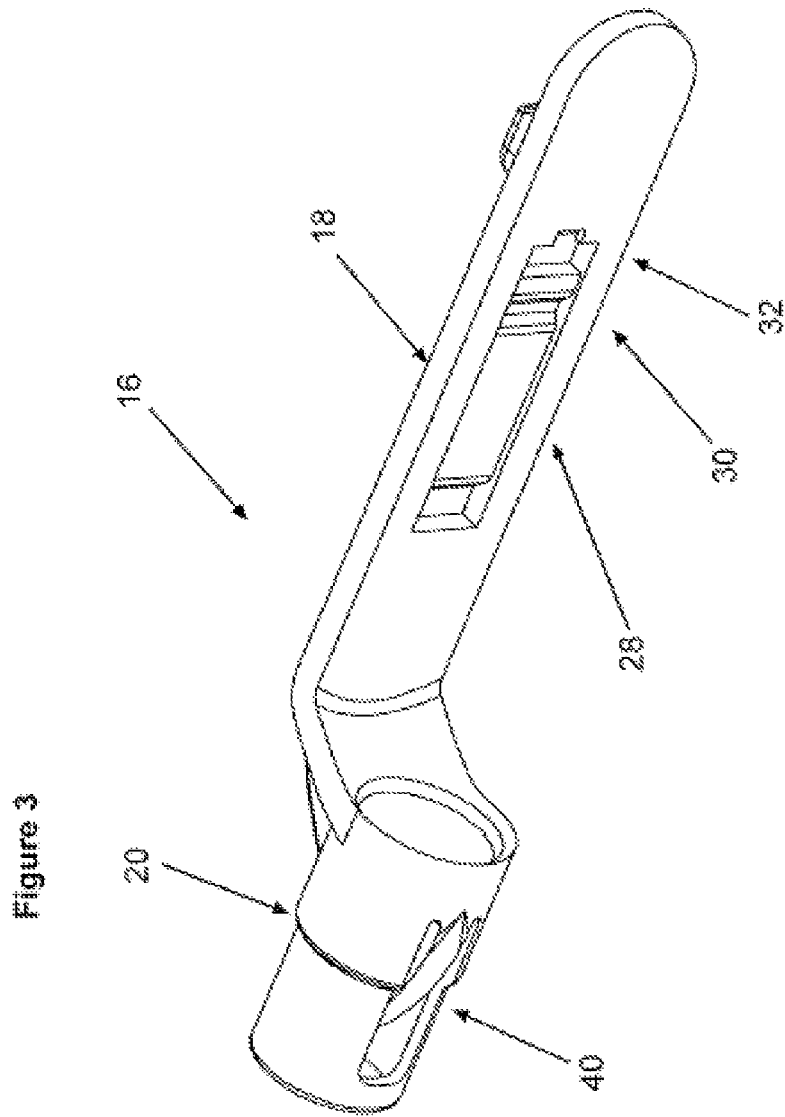
FIG. 3 shows a side view of one embodiment of the needle guard.

FIG. 3 shows a side view of a needle guard 16 according to one embodiment of the present invention. The needle guard 16 comprises an elongate member 18 and a cylindrical guard 20. The cylindrical guard 20 is at the distal end of the elongate member 18. In a preferred embodiment, the elongate member 18 may be L-shaped, although other shapes may be used. For example, the elongate member 18 may be C-shaped. In all embodiments of the present invention the length of the elongate member 18 is longer than the length of the needle (not shown) to be used with the needle guard. In a further embodiment, the elongate member 18 comprises one or more recesses 28 on the underside of the elongate member 18. In a preferred embodiment, the elongate member 18 comprises a first 30 and second recess 32, wherein both recesses 28 are proximally positioned on the elongate member 18, and wherein the second recess 32 is proximally positioned with respect to the first recess 30. In a preferred embodiment, the second recess 32 is deeper than the first recess 30. In a further aspect of the present invention, the needle guard 16 further comprises a resilient member 40. In one embodiment the member is an inwardly extending portion of the cylindrical guard 20.

Figure 4:
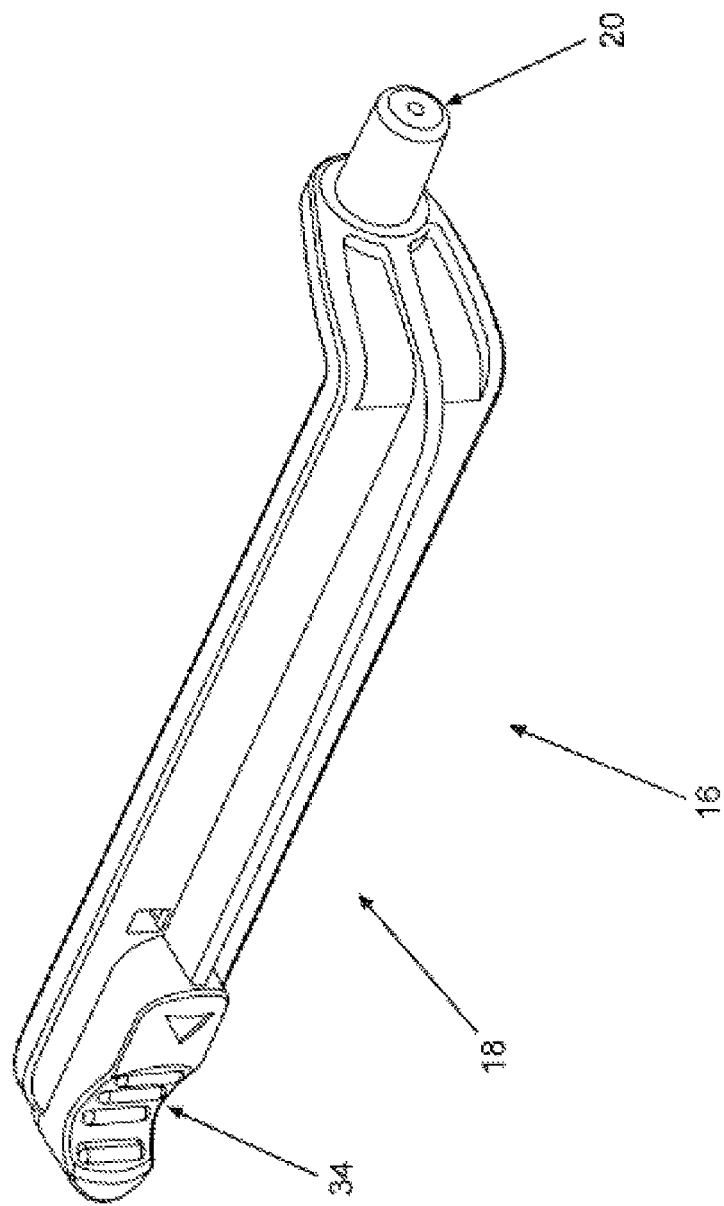
FIG. 4 shows an alternative side view of one embodiment of the needle guard.

FIG. 4 shows an alternative side view of a needle guard 16 according to one embodiment of the present invention, comprising an elongate member 18 and a cylindrical guard 20. The elongate member 18 also comprises a disengagement means 34. In this embodiment the disengagement means 34 comprises a finger shaped groove on the proximal end of the elongate member 18. In use, application of digital pressure to the finger shaped groove 34 in an axial direction—proximal or distal—is sufficient to disengage the projection on the needle guard supporting member (not shown) from the first recess (not shown) on the elongate member 18 and restore axial movement of the needle guard 16. The finger shaped groove 34 may also be ribbed to improve grip on the groove when in use.

Figure 5:
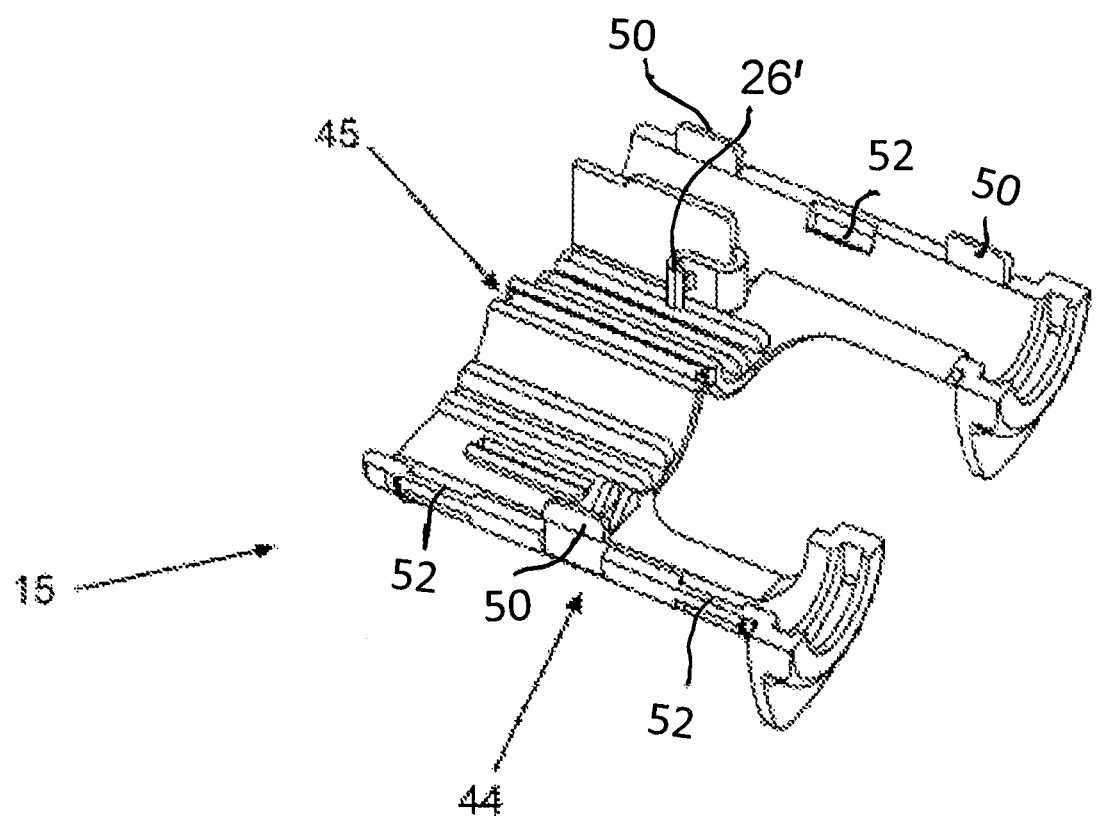
FIG. 5 shows a top view of one embodiment of the needle guard supporting member.
Figure 6:
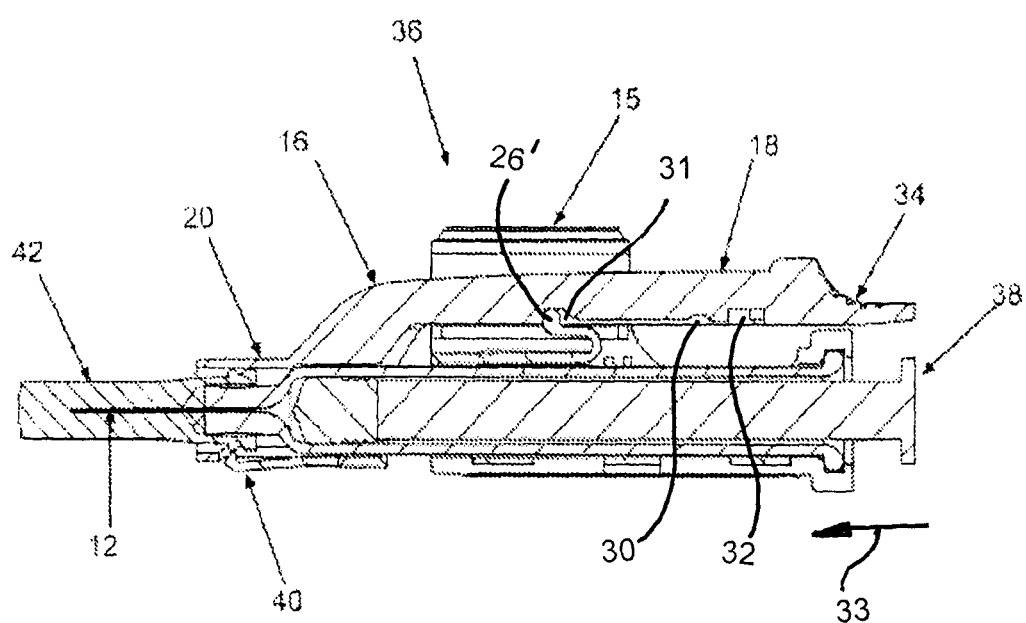
FIG. 6 shows a cross-section of one embodiment of the needle assembly. In this embodiment the injecting or collecting means is a staked needle syringe.

FIG. 5 shows a top view of a needle guard supporting member 15 according to one embodiment of the present invention. The needle guard supporting member 15 may comprise a hinge 45 to allow the needle guard supporting member 15 to be opened outwards along its longitudinal axis. In its open configuration, as shown in this embodiment, the needle guard supporting member 15 is configured to receive a syringe 38 (FIG. 6) and the needle guard 16 (FIG. 6). Through operation of the hinge 45 the guard supporting member 15 can then be closed around the syringe and needle guard 16. The guard supporting member 15 may further comprise a locking means 44 to maintain the guard supporting member in a closed configuration. The locking means 44 may comprise a latch, clip or snap-fit locking mechanism. In this embodiment the locking means 44 is a snap fit locking mechanism depicted by a detent mechanism comprising male detent elements 50 and mating female elements 52. Other locking means will be known to the skilled person.

Figure 7:
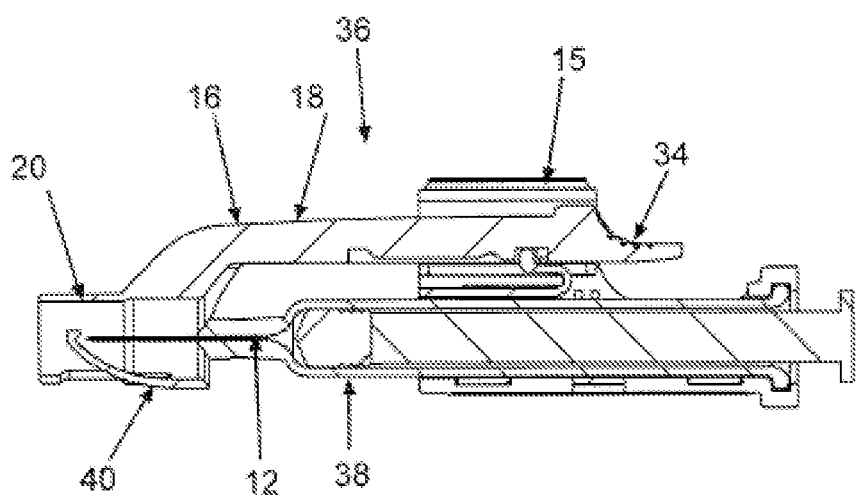
FIG. 7 shows a cross-section of one embodiment of the needle assembly. In this embodiment the injecting or collecting means is a staked needle syringe.
Figure 10:
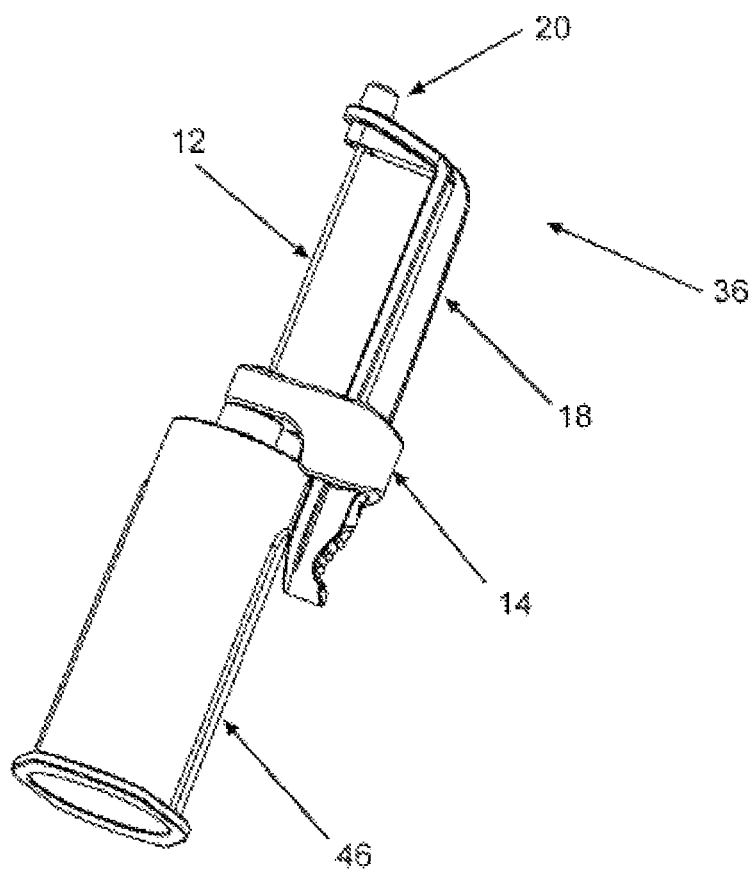
FIG. 10 shows a perspective view of an alternative embodiment of the needle assembly wherein the needle is a blood collection needle and the collecting means is a tube holder

FIGS. 6 and 7 show a cross-section view of a needle assembly 36 according to one embodiment of the present invention, comprising a needle guard 16 comprising an elongate member 18 having a disengagement means 34 and cylindrical guard 20 having a resilient member 40, a needle guard supporting member 15, a needle 12 covered by a needle cap 42 and a syringe 38. In preparation for use, the needle 12, and needle cap 42 if present, are passed through the lumen of the cylindrical guard 20. The needle guard supporting member 15 is then attached to the syringe 38 and elongate member 18 by closure of the hinged portion (not shown) of the needle guard supporting member 15. This allows the needle guard to be retrofitted to connected syringes. In FIG. 6, the needle assembly 36 is in the default position with the needle cap 42 over the needle tip 12 and the needle guard 16 in the retracted position (FIG. 6). In this position, the resilient member 40 is in the inactive position (not protecting the tip of the needle 12). In this embodiment, the resilient member 40 is maintained in the inactive position through engagement with the needle cap 42. Projection 26' (FIGS. 5 and 6) on the guard supporting member 15 selectively engages one of the recesses 30 and 32 (FIG. 6) in the needle guard 16 when the needle guard 16 is displaced in the axial direction 33, FIG. 6, The projection 26' is resilient to displace in and out of the respective recesses. In FIG. 6, the projection 26' is in its acquiescent position in recess 31 in the needle guard 16. When the guard 16 is moved forward in direction 33, the projection 26' displaces out of recess 31 until it engages a selective one of recesses 30 and 32. Recess 30 is shallower than recess 32 such that the projection can disengage from recess 30 with a lower force than from recess 32. Recesses 31 and 32 have inclined side walls to permit the projection 26' to easily disengage from the corresponding recess in response to a disengagement force in direction 33 (FIG. 6). The recess 32 has side walls that are normal to its bottom wall for providing a relatively high disengagement force on the guard 16 to lock the guard in this needle safety position when the projection 26' is engaged therewith. Recess 30 is provided to permit the guard to protect the needle in a temporary position so the guard can be move to its acquiescent position to permit multiple collection tubes 46 (FIG. 10) to be used while protecting the needle tip as the tubes are loaded and interchanged with the needle assembly 36 (FIG. 10). FIG. 7 shows the resilient member 40 in the active position. In this position the resilient member 40 covers the needle tip 12. In this embodiment, movement of the needle guard 16 from the first to the second position causes the resilient member 40 to move from the inactive to the active position. The resilient member 40 may be formed from a portion of the cylindrical guard 20. The resilient member 40 may also be attached to the interior of the cylindrical guard 20. The resilient member 40 may be curved although other shapes will be known to the skilled person. The resilient member may also comprise a distally positioned hook configured to engage with at least one of the needle cap 42 and needle tip 12.

Figure 8:
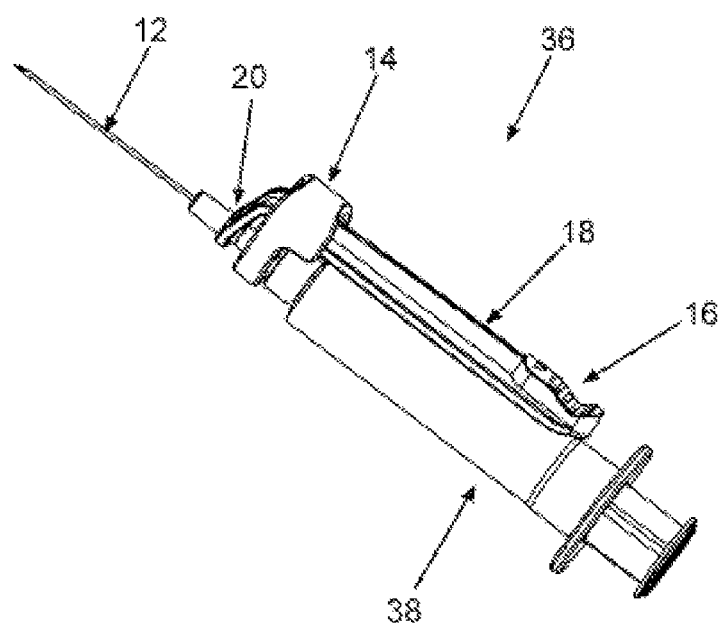
FIG. 8 shows a perspective view of one embodiment of the needle assembly showing the needle guard in a retracted position with the needle tip exposed. In this embodiment the needle is a conventional hypodermic needle and the injecting means is a conventional syringe.
Figure 9:
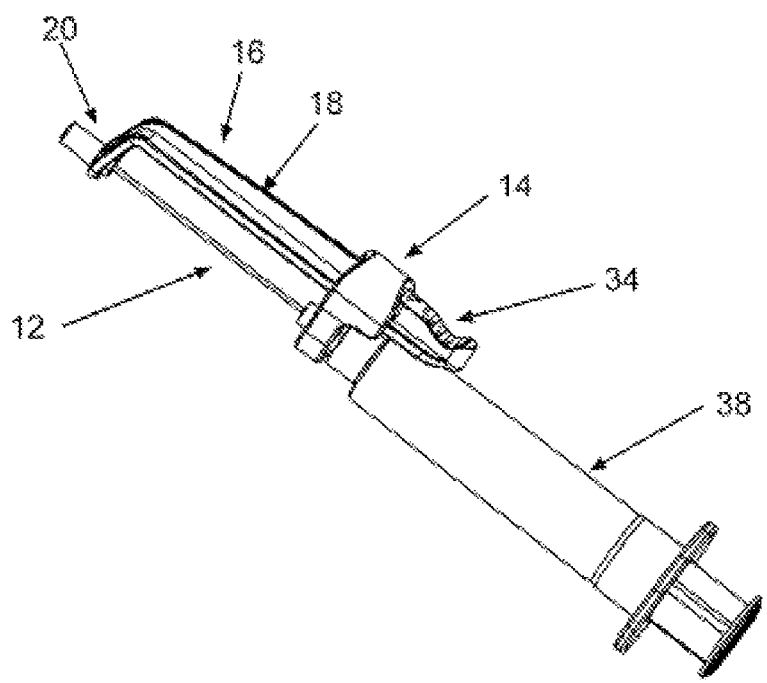
FIG. 9 shows a perspective view of one embodiment of the needle assembly showing the needle guard in an extended position with the needle tip covered. Again, in this embodiment the needle is a conventional hypodermic needle and the injecting means is a conventional syringe.

FIGS. 8 and 9 show a perspective view of a needle assembly 36 according to one embodiment of the present invention, comprising a needle 12 having a needle hub and needle tip, a needle guard 16 comprising an elongate member 18 and a cylindrical guard 20, a needle guard supporting member 14 and a syringe 38, wherein the elongate member 18 is axially slideable with respect to the needle guard supporting member 14. In one embodiment of the present invention the guard supporting member 14 is engageable with the hub of the needle 12. The needle 12 may be attached to an injecting or collecting means, such as a conventional syringe 38, by a luer lock—although other types of connection known to the skilled person may be used. FIG. 8 shows a needle assembly 36 ready for use wherein the needle guard 16 is retracted and the needle tip is exposed. From this position the needle guard can be easily extended to cover the needle tip without the user having to place their hands in close proximity to the needle tip. The user may move the needle guard distally by applying digital pressure in an axial direction to the finger shaped groove 34. FIG. 9 shows the needle assembly of FIG. 8 wherein the needle guard 16 is extended to cover the needle tip. The needle guard 16 may be retracted using the disengagement means 34 when the needle guard 16 is in the first locked position.

FIG. 10 shows a perspective view of an alternative embodiment of the present invention. This figure shows a needle assembly 36 comprising a needle 12 having a needle tip and hub, a needle guard support member 14 engageable with the needle hub and a needle guard, comprising an elongate member 18 and cylindrical guard 20. In this embodiment the needle 12 is a multi blood collection needle 12 attached to a vacuum collection tube 46.

Figure 11:
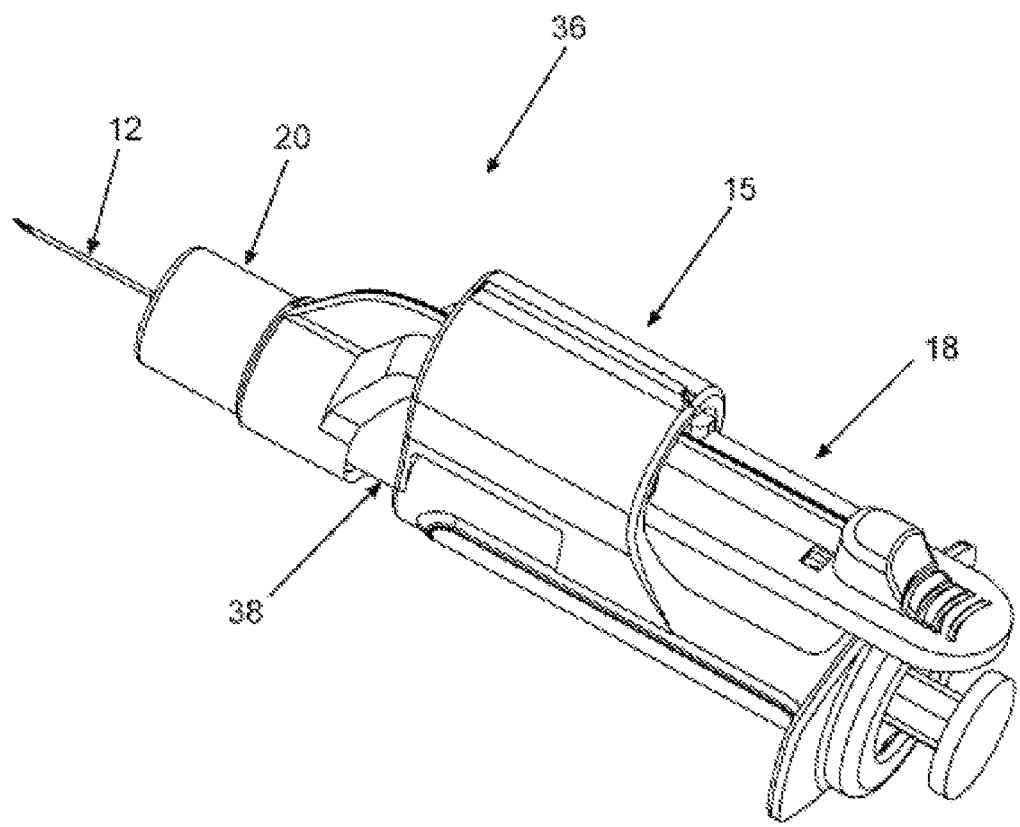
FIG. 11 shows a perspective view of an alternative embodiment of the needle assembly of the present invention, wherein the needle guard support member is engageable with the syringe. In this embodiment the injecting means is a staked needle syringe.

FIG. 11 shows an alternative view of the embodiment of FIG. 6 wherein the needle cap has been removed and the needle assembly 36 is ready for use. In this embodiment the needle guard supporting member 15 is engageable with the syringe 38 and the elongate member 18 of the needle guard 16.

The invention claimed is:

1. A needle safety lock comprising:
a needle guard supporting member;
a needle guard comprising an elongate member coupled to said needle guard supporting member and axially slidable with respect to said needle guard supporting member, said needle guard further comprising a cylindrical guard located at a distal end of the elongate member and having two open ends to enclose at least a portion of a needle, wherein said elongate member is longer than the length of said needle, and wherein a disengagement member is provided, proximally positioned on the elongate member, and said needle guard is axially slidable with respect to said needle from a first position wherein the tip of said needle is exposed, to a second position wherein the tip of said needle is covered, by application of digital pressure in an axial direction to the disengagement member;
a lock to secure said needle guard in a first locking position that is releasable and a second locking position that is non-releasable, wherein the position of said needle guard in both the first and second locking positions corresponds with the position of said second position wherein the tip of said needle is covered, wherein said lock comprises a projection on one of said needle guard supporting member or elongate member, and first and second recesses on the other of said needle guard supporting member or elongate member, wherein engagement of said projection and said recesses prevent axial movement of said needle guard selectively when the needle guard is in said second position wherein the tip of said needle is covered.

2. A needle guard safety device comprising a needle having a needle tip and hub; and having the needle safety lock of claim 1 fixed to the needle hub.

3. The needle guard safety device of claim 2, wherein said needle guard supporting member is engageable with the hub of said needle.

4. A needle assembly comprising the needle guard safety device of claim 2 and one of a syringe or a collection tube wherein said needle guard supporting member is engageable with the syringe or collection tube.

5. The needle safety lock of claim 1, wherein the projection is provided on said needle guard supporting member.

6. The needle safety lock of claim 1, wherein said elongate member comprises a first and second recess for engagement with said projection wherein said first and second recesses are spaced axially to provide said first and second locking positions that prevent axial movement of said needle guard when the needle guard is in said second position.

7. The needle safety lock of claim 6, wherein said recesses are positioned proximally on the elongate member.

8. The needle safety lock of claim 6, wherein said first and second recesses are arranged such that said first recess restricts axial movement up to application of a first predefined force, and said second recess restricts axial movement up to a second greater predefined force.

9. The needle safety lock of claim 1, wherein said cylindrical guard further comprises a resilient member.

10. The needle assembly of claim 4, wherein the syringe is a staked needle syringe and the collection tube is a blood collection tube.

11. The needle guard safety device of claim 2, wherein said needle is a hypodermic needle, surgical needle, tuohy needle or blood collection needle.

12. The needle safety lock of claim 7 wherein the second recess is spaced proximally from the first recess.

13. The needle safety lock of claim 1 wherein the needle guard supporting member is configured to open to receive a syringe.

14. The needle safety lock of claim 13 wherein the needle guard supporting member includes a hinge configured to permit opening of the needle guard supporting member.

15. The needle safety lock of claim 14 wherein the needle guard supporting member includes a lock to selectively maintain the needle guard supporting member in a closed configuration.

\* \* \* \* \*